Jan. 19, 1954 F. MEILLAND Plant Pat. 1,244
ROSE PLANT
Filed Jan. 19, 1953
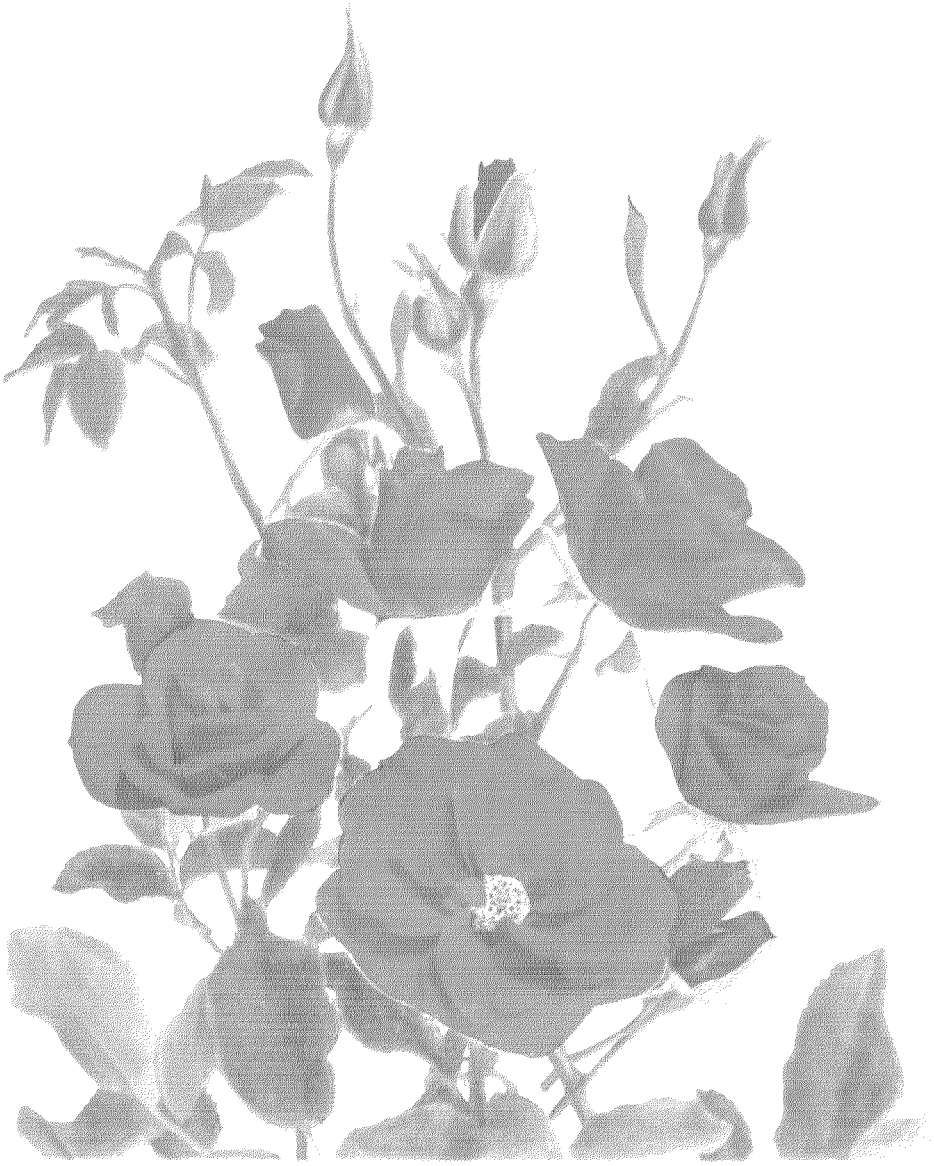
Inventor
Francis Meilland
By Cobb & Cobb
Attorneys Patented Jan. 19, 1954 Plant Pat. 1,244

UNITED STATES PATENT OFFICE 1,244

ROSE PLANT

Francis Meilland, Cap Azura, Cap d'Antibes, France, assignor to The Conard-Pyle Company, West Grove, Pa., a corporation of Pennsylvania Application January 19, 1953, Serial No. 332,136

1 Claim. (Cl. 47—61)

The present invention relates to a new and distinct variety of rose plant of the hybrid polyantha class which was originated by me by crossing the variety "Alain" (unpatented) with the variety "Floradora" (unpatented).

My new variety is most particularly distinguished from its parents, as well as from all other varieties of its class, by the unusual and marked permanence or fixity of the intense red color of its blooms which are characterized by an unusual intensity of scarlet suffusion which most nearly corresponds to Spectrum Red in color, but more intense and somewhat beyond the range of the usual standard color charts.

In addition to this feature, my new variety is still further distinguished from other varieties by the general superiority of the characteristics of the plant and blooms, together with its more reliable habit of continuous blooms which make the new variety especially desirable for use in home gardens, as well as for commercial production.

Contrary to the color changes which occur in most red roses, the color of the blooms of my new variety does not change appreciably during bloom development or aging, nor by reason of any extreme weather conditions. In the locality of West Grove, Pennsylvania, U. S. A., the color remains constant from June through October, irrespective of long wet spells or blazing sunshine, and the color has never been observed to fade or tend to "blue" in the manner that is a common occurrence in most other red roses.

Asexual reproduction of my new variety by budding in France, as well as at West Grove, Pennsylvania, U. S. A., shows that the foregoing characteristics come true to form and are established and transmitted through succeeding propagations.

The accompanying drawing shows typical specimens of the flowers and foilage of my new variety in different stages of development.

The following is a detailed description of my new variety, with color terminology in accordance with Ridgway's Color Standards and Nomenclature, except where general color terms of ordinary dictionary significance are obvious:

Type: Hardy; bush; seedling; for cut-flowers and for garden decoration.

Class: Hybrid polyantha.

Breeding: Seedling.

*Seed parent.*—"Alain."

*Pollen parent.*—"Floradora."

Propagation: Holds its distinguishing characteristics through succeeding propagations by budding.

*Flower*

Locality where grown and observed: West Grove, Pennsylvania, U. S. A.

Flowers borne: Several to stem; in irregular cluster; on strong, medium length stems.

Quantity of bloom: Abundant, outdoors.

Continuity: Continuous.

Fragrance: Slight.

Bud:

*Peduncle.*—Medium length; medium caliper; erect; almost smooth; few red prickles. Color—Maroon, Plate I; sometimes tinged with light green on under side.

*Before calyx breaks.* — Size — medium. Form—pointed-ovoid; with foliaceous appendages on the surface of the bud; with medium cut foliaceous parts extending beyond the tip of the bud equal to about ¾ of its length.

*As calyx breaks.*—Color—Oxblood, Plate I.

*As first petal opens.*—Size—medium. Form—medium length; cup-shaped. Color—outside: Carmine, Plate I, shaded with Oxblood Red, Plate I; inside: Carmine, Plate I, shading to Spectrum Red, Plate I, with ring of Hellebore Red, Plate XXXVIII at base of petal.

*Opening.*—Opens up well.

Bloom:

*Size, when fully open.*—Medium; from 2 inches to 2½ inches.

*Petalage.*—Semi-double; from 12 to 17 petals; arranged regularly.

*Form.*—Cupped at first; becoming open-cupped; petals being at first loosely cupped; remaining at maturity loosely cupped.

Petals: Medium thickness; with inside velvety and outside shiny.

*Shape.*—Outer—obovate; sometimes with 1, 2 or 3 notches. Intermediate—obovate; sometimes with 1 or 2 notches. Inner—obovate; generally with 1 notch.

This description of a newly opened flower was made from a rose grown outdoors in the month of October, at West Grove, Pennsylvania, U. S. A.:

*Color.*—outer petal—outside surface: Narrow band of Rose Color, Plate XII at base, shading into Carmine, Plate I; inside surface: Rose Red, Plate XII at base, shading into Spectrum Red, Plate I, and then into Carmine, Plate I. Intermediate petal—outside surface: Rose Red, Plate XII at base, shading to Carmine, Plate I; inside surface: Spinel Red, Plate XXVI at base, shading to Deep Spectrum Red, Plate I, and then into Nopal Red, Plate I at outer edge. Inner petal—outside surface: Hellebore Red, Plate XXXVIII at base, shading to Carmine, Plate I; inside surface: Daphne Red, Plate XXXVIII at base, shading to deeper than Spectrum Red, Plate I.

This description was made from a rose that was open for three days outdoors in the month of October, at West Grove, Pennsylvania, U. S. A.:

*Color.*—Outer petal—outside surface: Spinel Red, Plate XXVI at base, shading to Carmine, Plate I; inside surface: Tyrian Pink, Plate XII at base, shading to Carmine, Plate I. Inner petal—outside surface: Rose Color, Plate XII, shading to Carmine, Plate I; inside surface: Rose Color, Plate XII at base, shading to deeper than Spectrum Red, Plate I and to Carmine, Plate I.

*General color tonality.*—Newly opened flower—a slightly darker red than Spectrum Red, Plate I, shading to Carmine, Plate I on edges. Three days open—slightly darker than Spectrum Red, Plate I, with center showing Rose Color, Plate XII.

*Behavior.*—Drop off cleanly.

*Flower longevity.*—cut roses grown outdoors and kept at living-room temperatures—7 days in October.

*Reproductive organs*

Stamens: Many; arranged regularly about pistils.

Filaments: Few; short, but sometimes varying to medium length. Color—reddish, with yellow color at base.

Anthers: All open at once; medium size; occasionally fused with a petaloid. Color—yellow.

Pollen: Moderate abundance. Color—Lemon.

Pistils: Medium number.

Styles: Uneven; medium length; medium caliper; bunched.

Stigma: Color—pale yellow.

Ovaries: All enclosed in calyx.

Hips: None.

Sepals: Permanent; medium length; spear-shaped.

Seeds: None.

*Plant*

Foliage:

*Leaves.*—Compound of 3 to 5 leaflets; abundant; medium size; moderately glossy.

*Leaflets.*—Shape—oval; apex acute; base round; margin simply serrate.

*Color.*—Mature—upper surface: Dark Dull Yellow-Green, Plate XXXII; under surface: Light Elm Green, Plate XVII. Young—upper surface: Principal color Hessian Brown, Plate XVIII, shading to Cedar Green, Plate VI; under surface: Light Hay's Maroon, Plate XIII, with Calla Green, Plate V border to rib.

*Rachis (the supporting stem of the compound leaf).*—Medium weight. Upper side — grooved; prickly. Under side—smooth, with occasional thorns.

*Stipules.*—Medium length; medium width; with medium length points turning out at at an angle of less than 45°.

*Disease.*—Resistant to mildew and blackspot, as determined by comparison with other varieties grown under comparable cultural conditions at West Grove, Pennsylvania, U. S. A.

Growth:

*Habit.*—Bushy; upright; much-branched.

*Growth.*—Free; vigorous.

*Canes.*—Moderately heavy.

*Main stems.*—Color—green; occasionally tinged with reddish brown. Thorns—several; medium length; straight; pointed downward; with medium length, oval base. Prickles—none. Hairs—none.

*Branches.*—Color—green, tinged with red on upper side to full red. Thorns—several; short to medium length; straight, but upper thorns tend to be hooked; pointed downward; with medium length, oval base. Prickles—few; color—red. Hairs—none.

*New shoots.*—Color—dull red, with green on under surface. Thorns—several; medium length to long; straight, but some hooked near tips; pointed downward; with medium length, oval base. Prickles—few; color—reddish. Hairs—none.

I claim:

A new and distinct variety of rose plant of the hybrid polyantha class, substantially as herein shown and described, characterized particularly as to novelty by the exceptional permanence and fixity of the intense Spectrum Red general color tonality of its blooms without appreciable change during development, aging and extreme weather conditions, by the general superiority of the plant and its blooms, and by its reliably continuous blooming habit.

FRANCIS MEILLAND.

No references cited.